US006546067B2

(12) United States Patent
Aradate et al.

(10) Patent No.: US 6,546,067 B2
(45) Date of Patent: Apr. 8, 2003

(54) RECONSTRUCTION AND SCAN OF 4D-CT

(75) Inventors: Hiroshi Aradate, Tochigi-ken (JP);
Yasuo Saito, Tochigi-ken (JP);
Katsuyuki Taguchi, Tochigi-ken (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/771,592

(22) Filed: Jan. 30, 2001

(65) Prior Publication Data

US 2002/0131544 A1 Sep. 19, 2002

(51) Int. Cl.$^7$ ................................................. A61B 6/03
(52) U.S. Cl. .......................................... 378/15; 378/901
(58) Field of Search ............................... 378/4, 15, 901

(56) References Cited

U.S. PATENT DOCUMENTS

| | | | |
|---|---|---|---|
| 4,649,555 A | 3/1987 | Matsubayashi | 378/4 |
| 5,513,237 A | 4/1996 | Nobuta et al. | 378/19 |
| 5,706,325 A * | 1/1998 | Hu | 378/146 |
| 5,784,481 A * | 7/1998 | Hu | 378/4 |
| 5,825,842 A | 10/1998 | Taguchi | 378/15 |
| 5,974,108 A | 10/1999 | Taguchi et al. | 378/4 |
| 5,999,587 A * | 12/1999 | Ning et al. | 378/4 |
| 6,014,419 A * | 1/2000 | Hu | 378/4 |
| 6,075,836 A * | 6/2000 | Ning | 378/17 |
| 6,148,056 A * | 11/2000 | Lin et al. | 378/4 |
| 6,298,110 B1 * | 10/2001 | Ning | 378/17 |

OTHER PUBLICATIONS

Crawford, C.R. et al., "Computed tomography scanning with simultaneous patient translation," *Med. Phys.*, vol. 17, No. 6, Nov./Dec. 1990, pp. 967–982.

Defrise, M., et al., "A Cone–Beam Reconstruction Algorithm Using Shift–Variant Filtering and Cone–Beam Backprojection," *IEEE Trans. On Med. Imaging*, vol. 13, No. 1, Mar. 1994, pp. 186–195.

Feldkamp, L.A., et al., "Practical cone–beam algorithm," *J. Opt. Soc. Am. A*, vol. 1, No. 6, Jun., 1984, pp. 612–619.

Kudo, H., et al., An Extended Completeness Condition for Exact Cone–Beam Reconstruction and Its Application, *IEEE Medical Imaging Conference*, Japan, 1994.

Kudo, H., et al., "Three–Dimensional Helical–Scan Computed Tomography Using Cone–Beam Projections," *IEICE (DII)*, vol. J74–D–II, No. 8, Aug., 1991, pp. 1108–1114.

Parker, D., "Optimal short scan convolution reconstruction for fanbeam CT," *Med. Phys.*, vol. 9, No. 2, Mar./Apr. 1982, pp. 254–257.

Silver, M., "A method for including redundant data in computed tomography," *M. Phys.*, vol. 27, No. 4, pp. 773–774.

* cited by examiner

*Primary Examiner*—David V. Bruce
(74) *Attorney, Agent, or Firm*—Oblon, Spivak, McClelland, Maier & Neustadt, P.C.

(57) ABSTRACT

A method, system, and computer-readable medium that can resolve continuous and/or relatively rapid changes with time of a volume V without deterioration in image quality. In one embodiment of this invention, a subset of the projection data collected along a continuous circular orbit is combined with projection data collected along a different orbit to reconstruct the volume V substantially as it was when the subset of the projection data was collected. In one embodiment, the different orbit is a linear or a helical orbit. Further, staggered subsets of the projection data collected along a continuous circular orbit can also be used, as can further projection data collected along a linear orbit to resolve continuous and/or relatively rapid changes of a volume V.

29 Claims, 12 Drawing Sheets

RECONSTRUCTION AND SCAN OF 4D-CT

BACKGROUND OF THE INVENTION

1. Field of the Invention

The invention relates to a CT X-ray apparatus, and more particularly to a scan and reconstruction method, device, and computer-readable medium when a dynamic scan is conducted in a CT X-ray apparatus radiating a cone beam.

The present invention includes use of various technologies referenced and described in the references identified in the appended LIST OF REFERENCES and cross-referenced throughout the specification by boldface numerals in brackets corresponding to the respective references, the entire contents of all of which are incorporated herein by reference.

2. Discussion of the Background

Figure 1A:
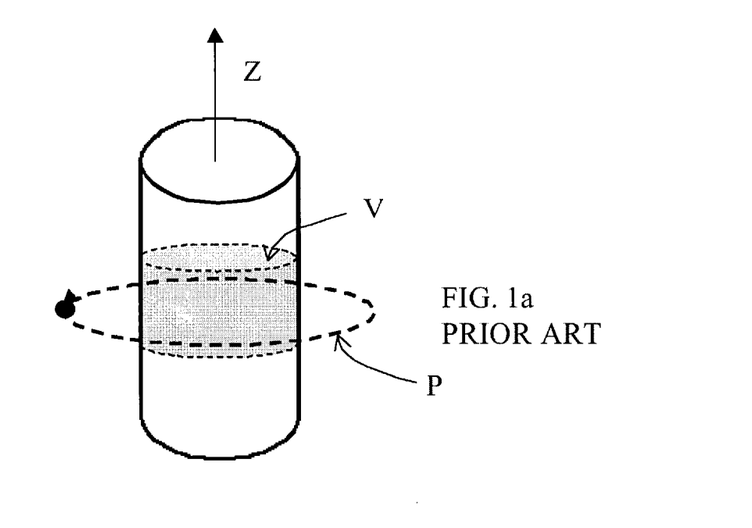
FIGS. 1a, 1b, and 1c are a conceptual diagram of circular orbital scan, a graph illustrating the time course of circular orbital scan, and a diagrammatic illustration of cone beam projection, respectively.
Figure 1B:
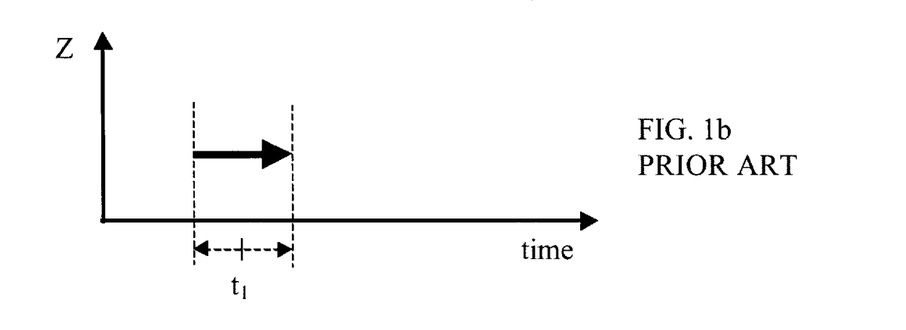
Figure 1C:
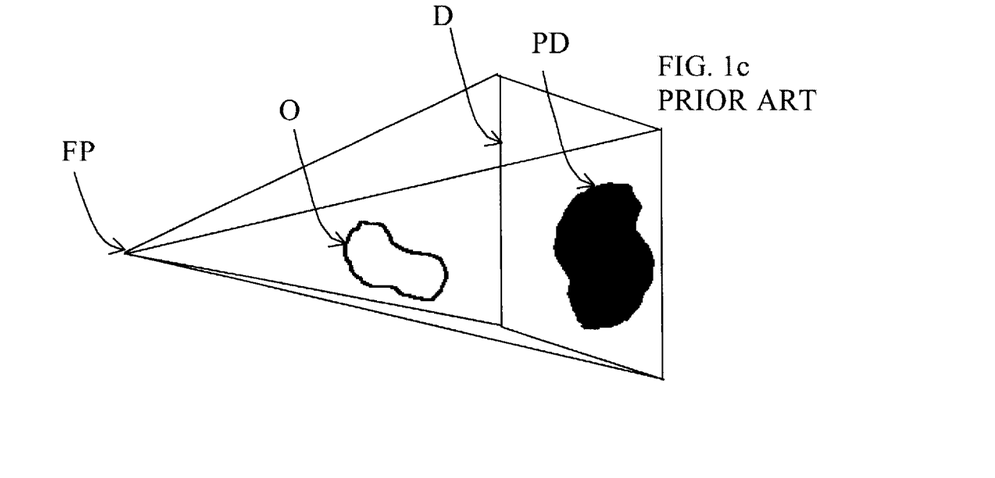

Cone-beam computed tomography (CT) reconstructs the interior of an object of interest or patient O from two-dimensional projections PD of X-rays transmitted through the object of interest or patient, as illustrated in FIG. 1c. An X-ray source FP and an X-ray detector D are arranged in a number of different positions so that X-rays transmitted through the object of interest O are received at the detector D. The detector D, either alone or in conjunction with other devices, generates image data for each position of the source and/or detector. The image data is then stored, manipulated, and/or analyzed to reconstruct the interior of the object. In a cone-beam CT system, the detector D is in the form of an array of X-ray sensing elements.

An approximate reconstruction method, the so-called Feldkamp reconstruction method, has been described [1, 2]. In Feldkamp reconstruction, the focal point of an X-ray is moved along an ideally circular orbit P around a completely immobile object or patient, and a volume V is reconstructed by using the collected cone beam projected data, as illustrated in FIGS. 1a and 1b. The Feldkamp reconstruction can be generally expressed as shown in Eq. 1, where the function $F_C(\cdot)$ indicates that projection data $p_C$ obtained along a circular orbit is processed to yield the Feldkamp reconstruction of the interior volume of the patient or object of interest V, where:

$$V|_{t=t1} = F_C(p_C|_{t=t1}) \quad \text{Eq. (1)}$$

$F_C(\cdot)$: method of processing projection data obtained along a circular orbit $p_C|_t$: projection data at time period t obtained along a circular orbit $V|_t$: volume to be reconstructed as it existed at time period t t1: data collection time period, i.e., an imaging time period As seen above, projection data along a circular orbit P is collected over a finite period of time t1 that is required for translating the X-ray source and detector, as well as integrating the received X-ray intensity. Since a single reconstruction of the volume V requires the use of data collected at different times within the period t1, any shifting of the patient or object of interest during imaging quickly degrades image quality.

Figure 2A:
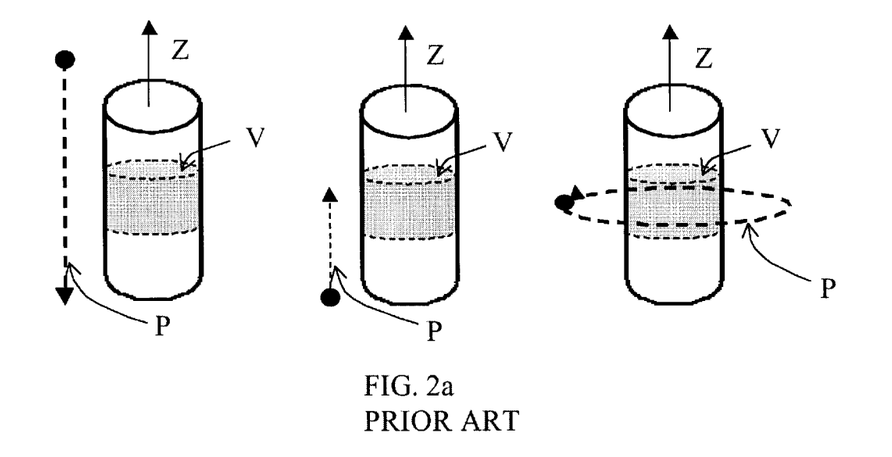
FIGS. 2a and 2b are a diagrammatic illustration of a (non-isokinetic) linear orbital scan followed by a circular orbital scan and a graph illustrating the time course of a linear orbital scan followed by a circular orbital scan, respectively.
Figure 2B:
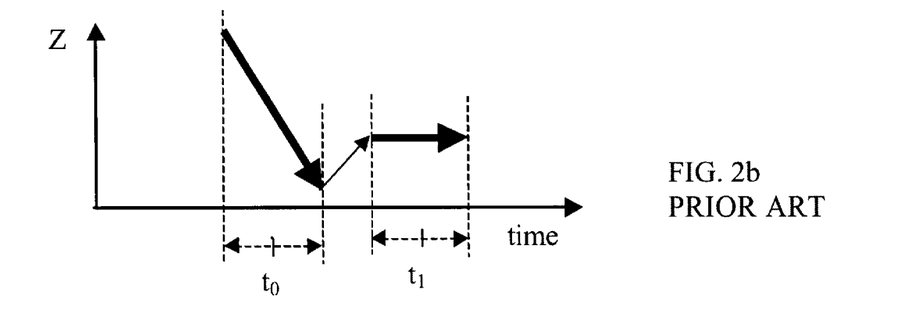
Figure 3A:
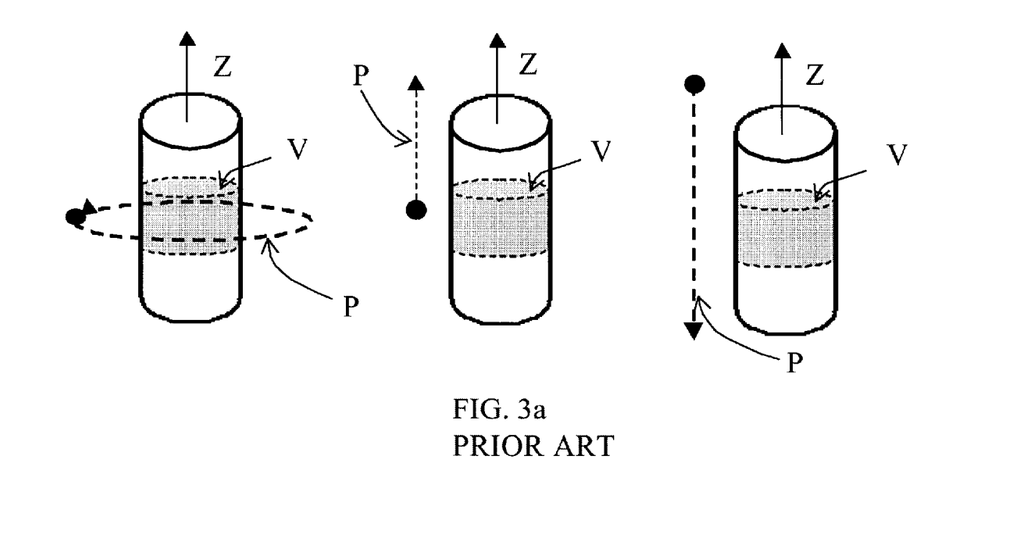
FIGS. 3a and 3b are a diagrammatic illustration of a (isokinetic) circular orbital scan followed by a linear orbital scan and a graph illustrating the time course of a circular orbital scan followed by a linear orbital scan, respectively.
Figure 3B:
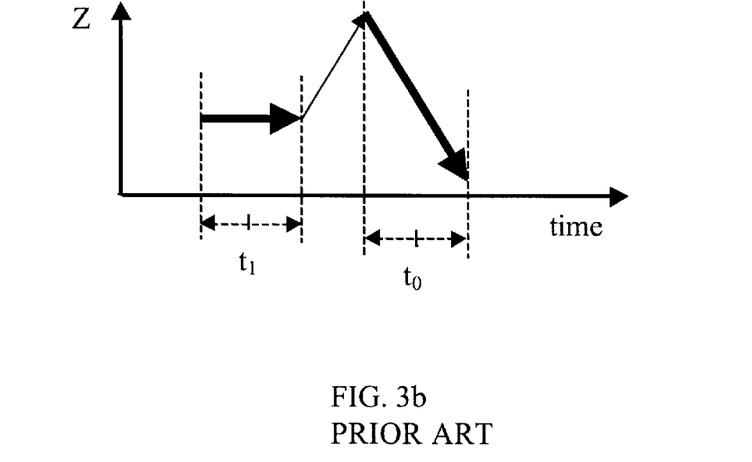

Even when the patient or object is completely immobile, when the cone angle becomes large, image artifacts in Feldkamp reconstruction are increased and the image quality deteriorates. In order to avoid this deterioration in image quality, other scan and reconstruction methods have been proposed [3a, 3b, 4]. A strict reconstruction method has been described in which the focal point of the X-rays is moved along linear and circular orbits P around a completely immobile patient or object of interest, and reconstruction is conducted by using the collected cone beam projected data [3a, 3b, 4], as illustrated in FIGS. 2a, 2b, 3a and 3b. As illustrated in FIG. 2b and hereinafter, orbits P where data is collected are denoted by arrows in bold type. These types of image reconstructions can be generally expressed as shown in Eq. 2, where the function $F_C(\cdot)$ indicates that projection data $p_C$ collected along the circular orbit is processed in a certain manner, and $F_L(\cdot)$ indicates that projection data $P_L$ collected along a linear orbit is processed in a certain manner. Although the function designation $F_C(\cdot)$ is the same as the function designation used as in Eq. 1, the two functions are not necessarily the same. Thus, $F_C(\cdot)$ in Eq. 2 is not necessarily the Feldkamp reconstruction, but rather only denotes the processing of data obtained along a "circular orbit."

$$V|_{t=t1} = F_C(p_C|_{t=t1}) + F_L(p_L|_{t=t0}) \quad \text{Eq. (2)}$$

$F_C(\cdot)$: method of processing projection data obtained along a circular orbit $F_L(\cdot)$: method of processing projection data obtained along a linear orbit $p_C|_t$: projection data at time period t obtained along a circular orbit $p_L|_t$: projection data at time period t obtained along a linear orbit $V|_t$: volume to be reconstructed as it existed at time period t Although the volume reconstructed by this method displays reduced deterioration in image quality, a problem still arises due to the finite times required for data collection. Typically, the linear orbit is scanned before (FIGS. 2a and 2b) or after (FIGS. 3a and 3b) the circular orbit. Moreover, since the berth that supports the patient or object is translated between the scan plane of the circular orbit and the scan starting position of the linear orbit (in the appropriate direction), an additional delay is required. This is indicated in Eq. 2 by the fact that the projection data obtained along a circular orbit $p_C$ is obtained over a time period t1, whereas the projection data obtained along a linear orbit $p_L$ is obtained over a time period t0. As a result, relatively rapid movements that occur within time periods shorter than the sum of t1 and t0 degrade image quality, and only very slow, intermittent movements can be resolved with this scan method, as illustrated in FIG. 5.

For the sake of convenience, the time period for collecting data along a (full or partial) circular orbit will hereinafter be referred to as $t_1, t_2, \ldots t_n$. Likewise, the time period for collecting data obtained along another (e.g., linear and/or helical orbit) will be referred to as $t_0$, regardless of which time period actually occurred first.

Other researcher have attempted to address the problem of relatively rapid (or continuous) movement during imaging by implementing cone-beam CT using projection data obtained from along a partial orbit of the object or patient. Such partial orbits are capable of providing complete image data for reconstruction of the interior of an object since many views in a complete circular orbit are redundant, i.e., the image data provide little or no new information. For example, if the object of interest is immobile and the system is ideal (i.e., no noise), switching the location of the source and detector will provide no new information along the ray through the axis even though image data from a second view has been collected.

A method for reconstruction of one particular partial orbit, namely an orbit that covers the "minimal complete data set" has been described in [6]. The "minimal complete data set" spans more than one half of a complete orbit. Namely, it spans 180° plus the maximum fan angle 2γm, where the maximum channel angle γm is the largest angle of a ray emitted by the X-ray source that is received at the X-ray detector relative to the ray emitted from the source that passes through the axis of rotation of the X-ray source and detector.

Another method for the reconstruction of a partial orbit is described [8].

Figure 4A:
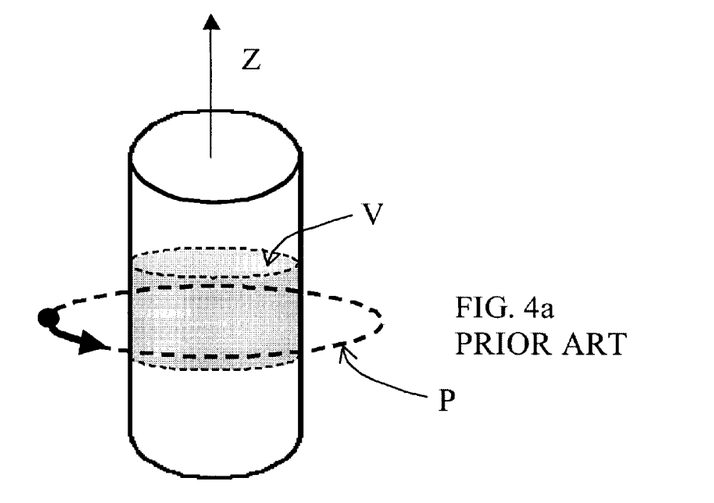
FIGS. 4a and 4b are a diagrammatic illustration of a continuous circular orbital scan and a graph illustrating the time course of a continuous circular orbital scan where partial orbits are excised from the continuous circular orbital scan staggered in time, respectively.
Figure 4B:
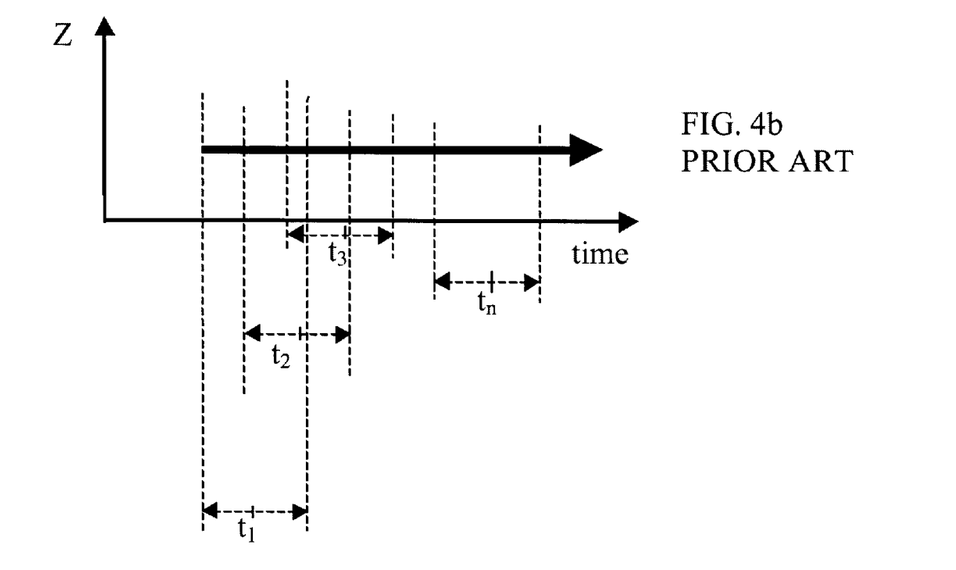
Figure 5A:
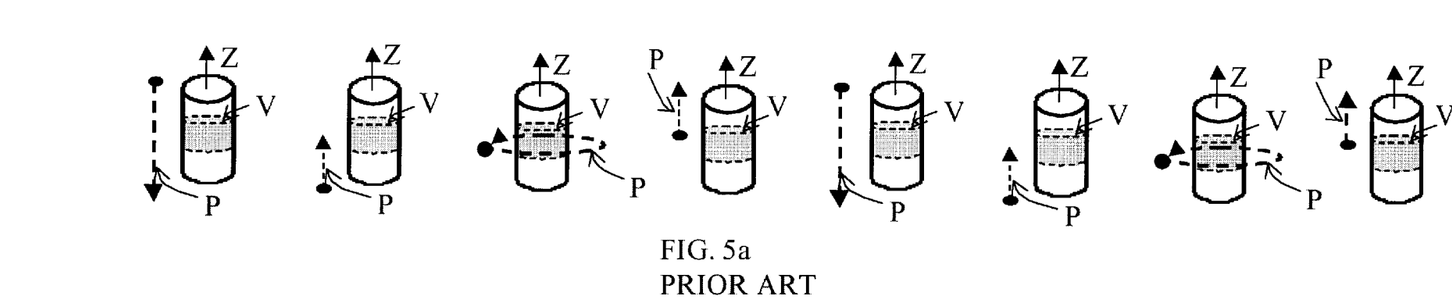
FIGS. 5a and 5b are a diagrammatic illustration of a linear scan followed by a (full or partial) circular orbital scan and a graph illustrating the time course of a linear scan followed by a circular orbital scan, illustrating the relatively long time period between images, respectively.
Figure 5B:
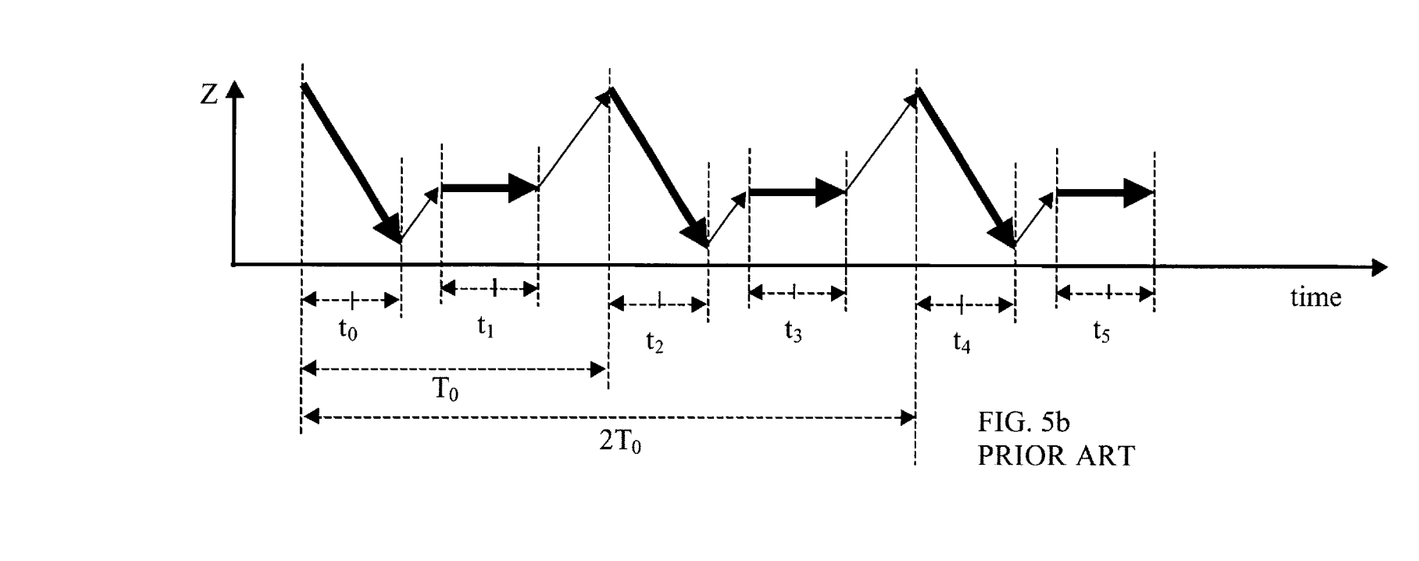

As illustrated in FIGS. 4a and 4b, plural partial and/or complete circular orbits can be excised from a continuous circular orbit P. As used herein, a "continuous circular orbit" need not extend into perpetuity, but rather indicates that several staggered partial and/or complete circular orbits can be excised from the scan. The "continuous circular orbit" illustrated in FIG. 4a and hereinafter is denoted by the undashed potion extending the circular orbit P beyond a single revolution. Once again, this is for illustrative purposes only, since a "continuous circular orbit" as used herein can actually span an angle smaller than one complete revolution if partial circular orbits are used for reconstruction. The collection times $t_1, t_2, \ldots t_n$ of the excised portions are staggered in time at relatively short increments so that relatively quicker and continuous movements can be imaged. However, reconstruction when the cone angle is large still suffers from the image degradation described above. When linear scans are inserted between even partial orbits as illustrated in FIGS. 5a and 5b, the resultant images still suffer under the same delays described in Eq. 2 and are only able to resolve slow, intermittent movements.

A need to resolve continuous and/or relatively rapid changes with time of the volume V without deterioration in image quality thus exists.

SUMMARY OF THE INVENTION

Accordingly, one object of this invention is to develop a method, system, and computer-readable medium that resolve continuous and/or relatively rapid changes with time of the volume V without deterioration in image quality.

This and other objects of the invention are realized through a method, system, and computer-readable medium that, in one embodiment of this invention, combine a subset of the projection data collected along a continuous circular orbit with projection data collected along a different orbit to reconstruct the volume V substantially as it was when the subset of the projection data was collected. In one embodiment, the different orbit is a linear or a helical orbit. Further, staggered subsets of the projection data collected along a continuous circular orbit can also be used in some embodiments, as can further projection data collected along a linear orbit to resolve continuous and/or relatively rapid changes of a volume V in some embodiments.

DETAILED DESCRIPTION OF THE PREFERRED EMBODIMENTS

Referring now to the drawings, wherein like reference numerals designate identical or corresponding parts throughout the several views, and more particularly to FIGS. 6a, 6b, 6c, 6d, and 6e thereof, wherein a diagrammatic illustration of a linear scan followed by a continuous circular orbital scan, a graph illustrating the time course of a linear scan followed by a continuous circular orbital scan, a diagrammatic illustration of a continuous circular orbital scan followed by a linear scan, a graph illustrating the time course of a continuous circular orbital scan followed by a linear scan, and a graph illustrating the time course of a linear scan interrupted by a continuous circular orbital scan are respectively provided.

As FIGS. 6a, 6b, 6c, 6d, and 6e illustrate, a scan of a linear orbit is made and the data collected along the linear orbit is combined with data from a continuous circular orbit. Since data can be excised from the continuous circular orbit scan, the data collected along the linear orbit is combined with data collected at an arbitrary time along the continuous circular orbit.

Figure 6A:
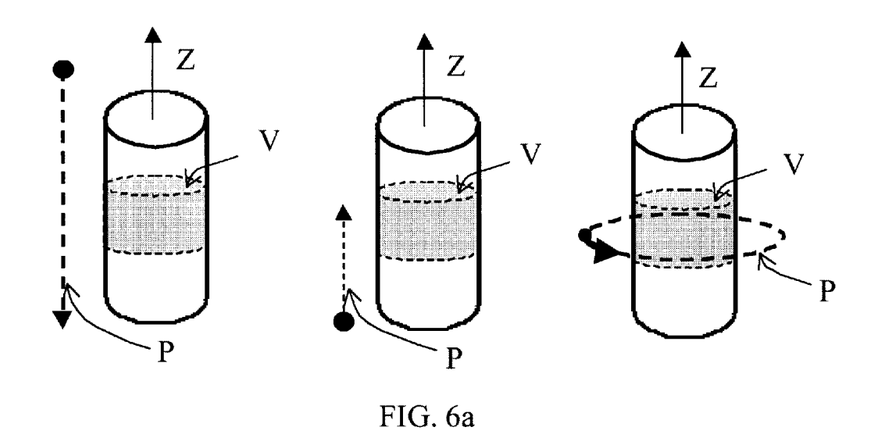
FIGS. 6a, 6b, 6c, 6d, and 6e are a diagrammatic illustration of a linear scan followed by a continuous circular orbital scan, a graph illustrating the time course of a linear scan followed by a continuous circular orbital scan, a diagrammatic illustration of a continuous circular orbital scan followed by a linear scan, a graph illustrating the time course of a continuous circular orbital scan followed by a linear scan, and a graph illustrating the time course of a linear scan interrupted by a continuous circular orbital scan, respectively.
Figure 6B:
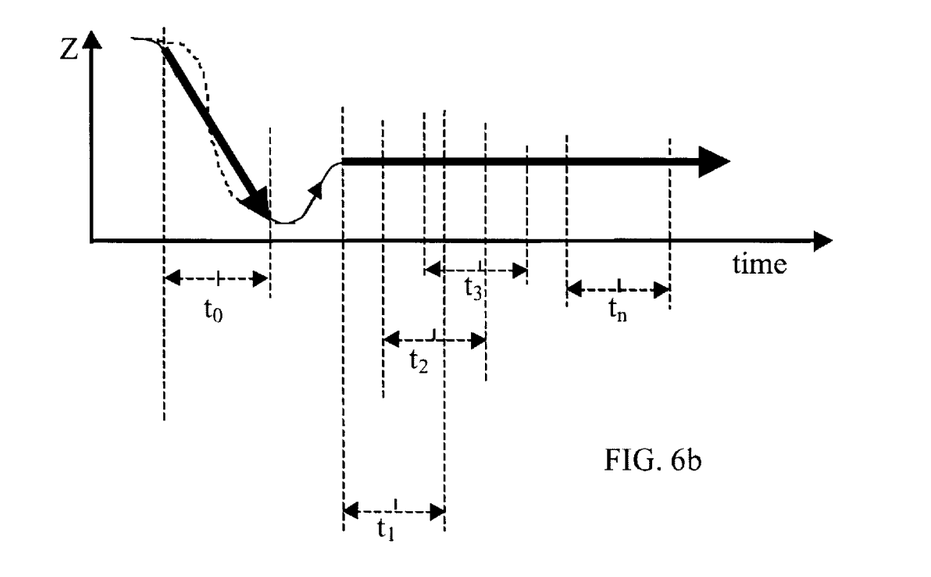

FIGS. 6a and 6b illustrate the situation where a linear orbit scan is performed first. First, projection data $p_L$ is collected along a linear orbit over a time period t0, and the scan along a circular orbit is then continuously conducted. In order to reconstruct the volume V at an arbitrary time, projection data $p_C$ corresponding to a complete or partial circular orbit collected over the corresponding time period t is excised from the projection data collected by the continuous circular orbit scan. By using this data and the collected projection data $P_L$ from the linear scan, the volume V can be reconstructed by the method described, e.g., in [3a, 3b, 4], as is generally expressed in Eq. 3. The projection data collected along the linear orbit over the time period t0 is used along with the projection data collected along the circular orbit at, e.g., the time periods t1, t, and tn, as illustrated in FIG. 6.

$$V|_t = F_C(p_C|_t) + w(t)F_L(p_L|_{t=t0}) \qquad \text{Eq. (3)}$$

$$[t0 < t1 \leq t \leq tn]$$

$F_C(\cdot)$: method of processing projection data obtained along a circular orbit $F_L(\cdot)$: method of processing projection data obtained along a linear orbit $p_C|_t$: projection data at time period t obtained along a circular orbit $p_L|_t$: projection data at time period t obtained along a linear orbit w(t): weighting coefficient for a time period t $V|_t$: volume to be reconstructed as it existed at time period t In many applications, the weighting coefficient w(t) for the set of projection data $p_L$ from a linear scan obtained over the time period t0 is equal to one. However, this is not necessarily the case, and the weighting coefficient w(t) can be adjusted to be less than one to, e.g., avoid overcorrection due to patient motion during the time between the linear scan and the circular scan.

Furthermore, although the weighting coefficient w(t) is described as for a time period t, several weighting coefficients may also be provided for each time period t. In other words, the weighting coefficient w(t) may be a function of time, rather than simply a function of the time period t.

Figure 6C:
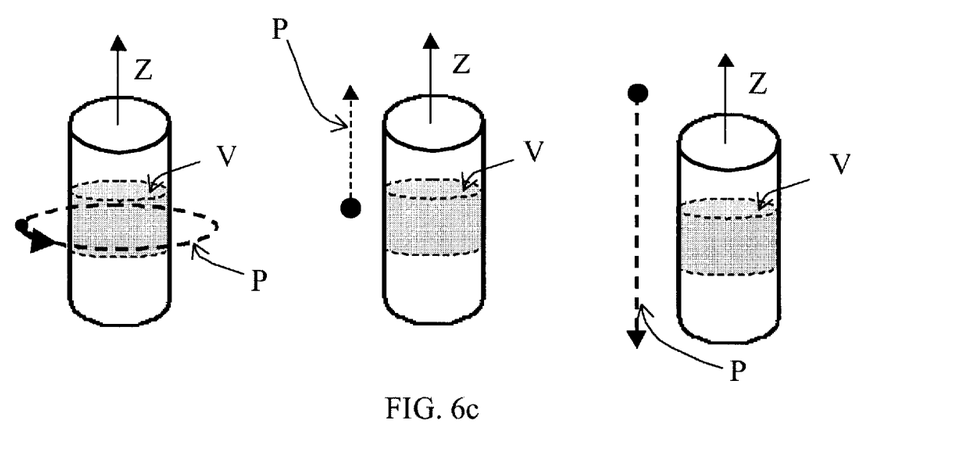
Figure 6D:
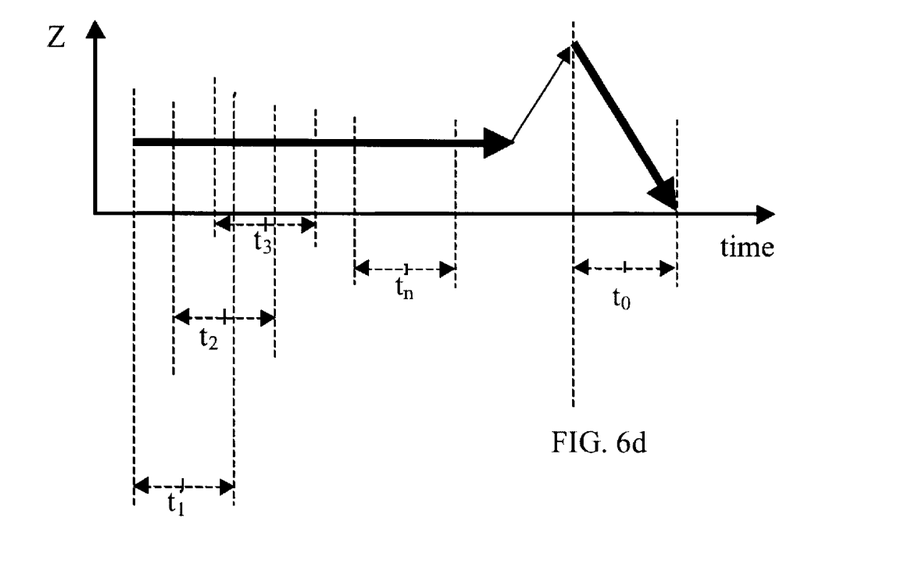
Figure 6E:
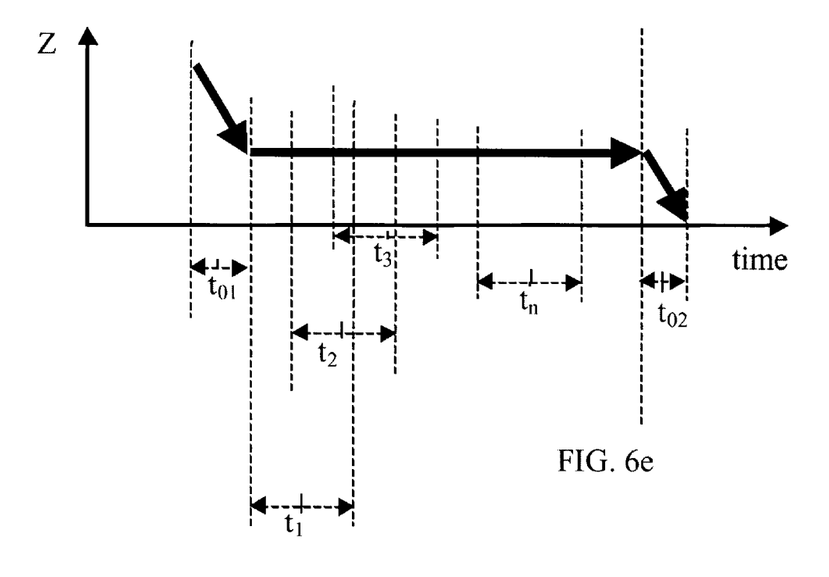

FIGS. 6a and 6b illustrate the situation where the scan of the linear orbit is conducted before the continuous scan of the circular orbit. The linear scans in FIGS. 6a and 6b, as illustrated, are non-isokinetic. Since the moving portions of the imaging device must accelerate and decelerate to and from the linear scan velocity, the edges of the linear scans are curved. This curvature is emphasized in FIG. 6b for illustrative purposes. FIGS. 6c and 6d illustrate the situation where the scan of the linear orbit is performed after the continuous scan of the circular orbit. FIGS. 6c and 6d, as illustrated, are non-isokinetic—the acceleration and deceleration is infinitely rapid. FIG. 6e illustrates the situation where a linear scan interrupted by a continuous circular orbital scan. For the sake of convenience, all scans herein except FIG. 6b are illustrated a non-isokinetic, although they may all be isokinetic or non-isokinetic. Thus, any of the scan orders and/or acceleration/deceleration profiles illustrated in FIGS. 6a, 6b, 6c, 6d, and 6e may be used as illustrated or in any further combination in accordance with the present invention.

The excised range of the projection data $p_C$ may be a complete circular orbit (one revolution), or other ranges may be used. For example, projection data obtained along more that one revolution may be used. In this case, e.g., Feldkamp reconstruction can be used if the projection data along the overlapping part of the orbits is weighted and summed, as given by Eqs. 6 and 7. As another example, projection data obtained along less than one revolution (partial orbit) may be used. As an example of this case, one half revolution plus the fan angle with weighted projection data, as described in references [6, 7, and 8], may be used.

$$p_e(\beta) = \begin{cases} w(\beta)p_e(\beta) + (1 - w(\beta))p_e(\beta + 2\pi) & [0 \leq \beta \leq \alpha] \\ p_e(\beta) & [\alpha < \beta \leq 2\pi] \end{cases} \qquad \text{Eq. (6)}$$

$$w(\beta) = \frac{\beta}{\alpha} \qquad \text{Eq. (7)}$$

Figure 7A:
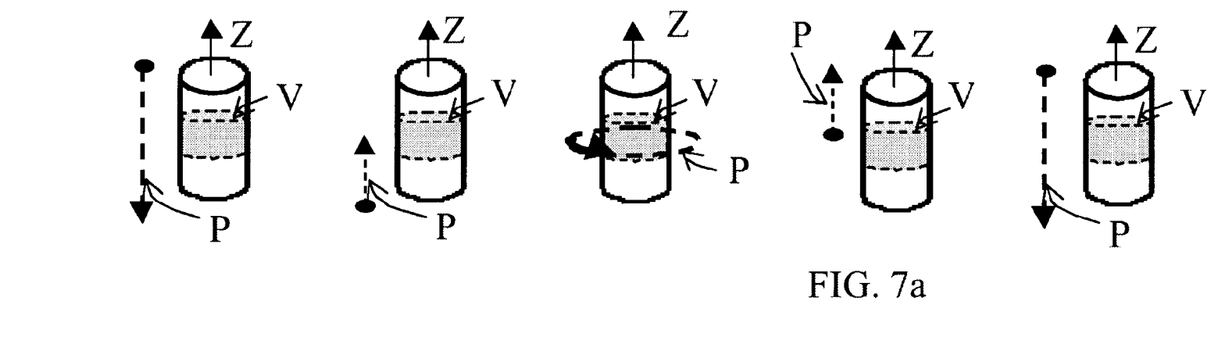
FIG. 7a is a diagrammatic illustration of the combination of linear orbital scans that are corrected at different times and circular orbital scan collected at different times.
Figure 7B:
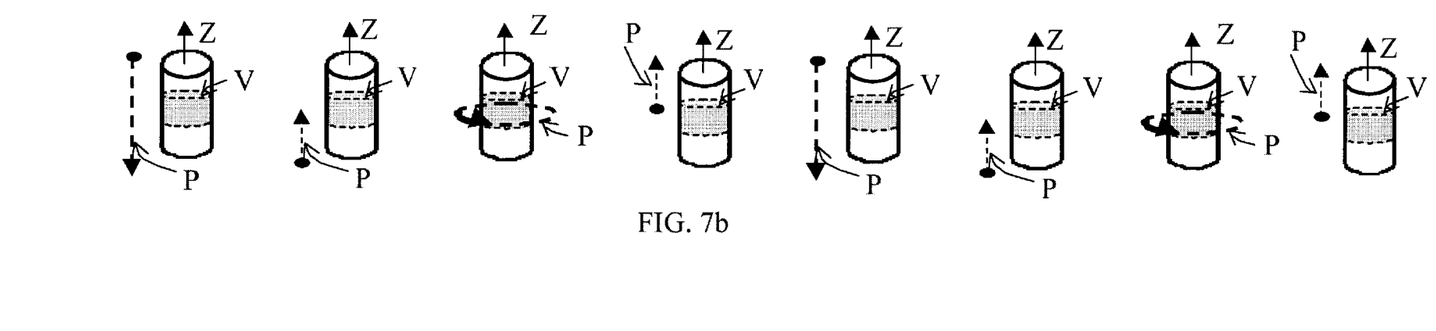
FIG. 7b is a diagrammtic illustration of repeating linear orbital scans and circular orbital scans by turns.
Figure 7C:
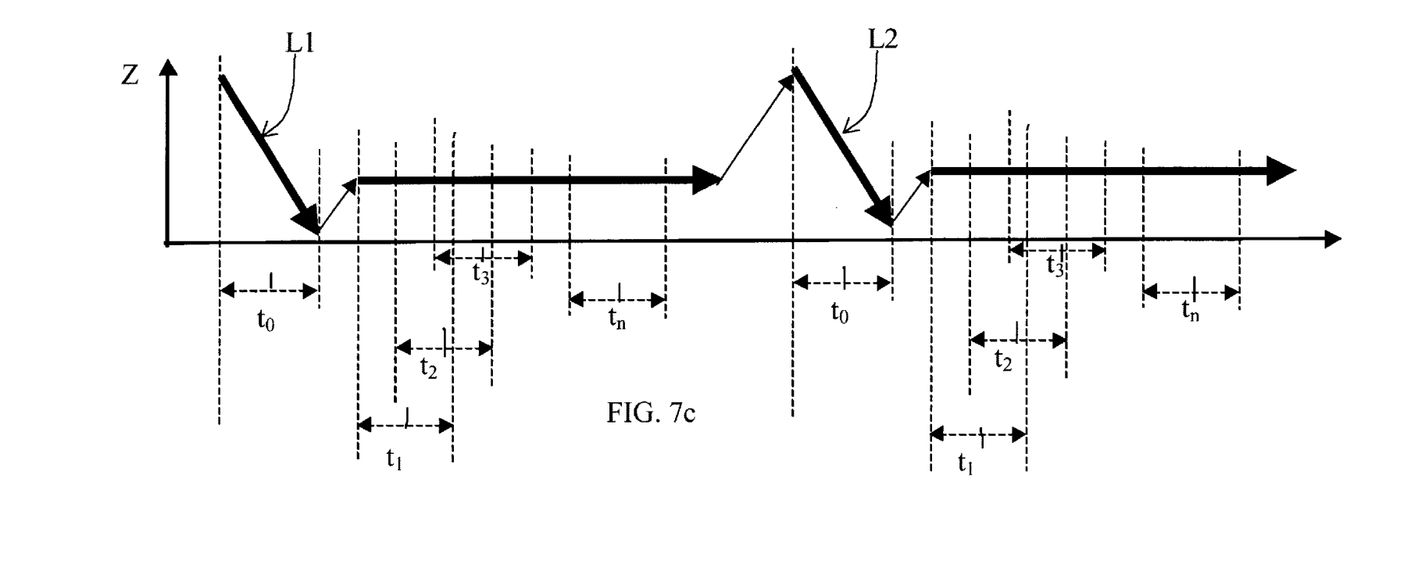
FIG. 7c is a graph illustrating the time course of the combination of linear orbital scans that are corrected at different times and circular orbital scan collected at different times.
Figure 8A:
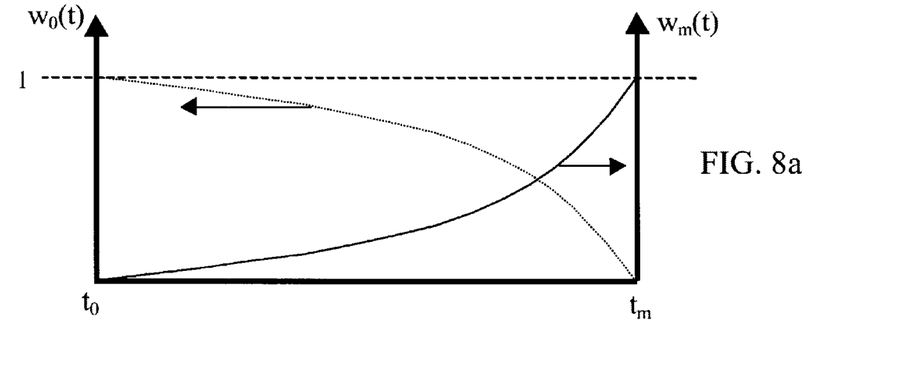
FIGS. 8a, 8b, and 8c are graphs showing the examples of the weighting coefficient w (t) of equation 5.
Figure 8B:
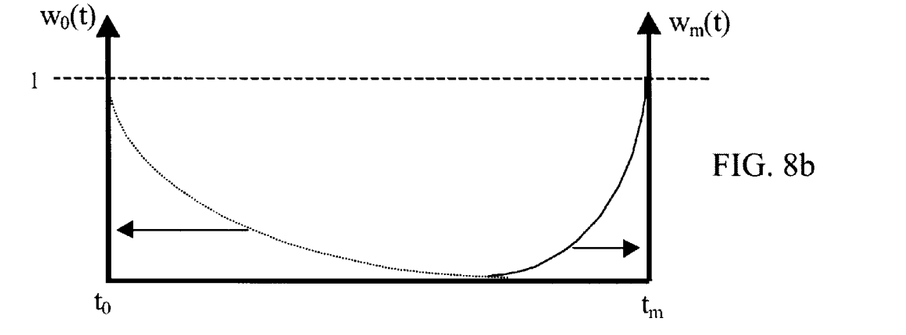
Figure 8C:
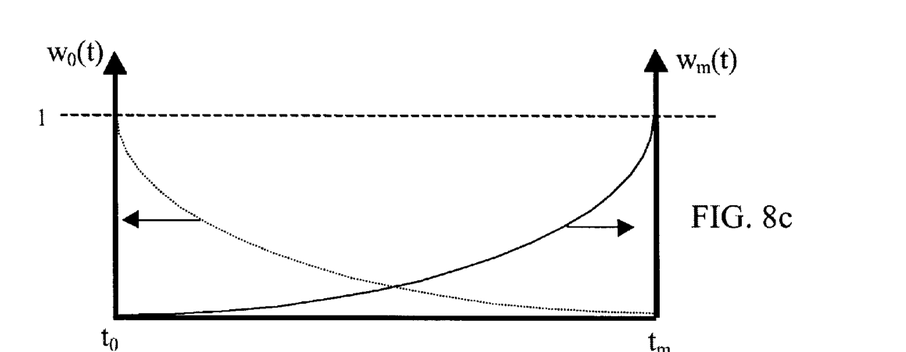

A second embodiment of the present invention uses the method described in Eqs. 4 and 5 to resolve continuous and/or relatively rapid changes with time of the volume V without deterioration in image quality. In this method, a linear orbital scan is first conducted and then followed by a continuous circular orbital scan. Once again, a continuous circular orbital scan need not be extended indefinitely to perform the present invention, but rather indicates that several staggered partial and/or complete circular orbits can be excised from the scan. Thus, after the continuous circular orbital scan has been performed for some time, it is in turn followed by a linear orbital scan. In this case, a weighted average of the two sets of projection data $p_L$ from the linear scans can be used, as expressed in Eq. 4 and Eq. 5, and illustrated in FIG. 7.

$$V|_t = F_C(p_C|_t) + (1 - w(t))F_L(p_L|_{t=t0}) + w(t)F_L(p_L|_{t=tm}) \qquad \text{Eq. (4)}$$

$$[t0 < t1 \leq t \leq tn < tm]$$

$$w(t) = \frac{t - t0}{tm - t0} \qquad \text{Eq. (5)}$$

$F_C(\cdot)$: method of processing projection data obtained along a circular orbit $F_L(\cdot)$: method of processing projection data obtained along a linear orbit $p_C|_t$: projection data at time period t obtained along a circular orbit $p_L|_t$: projection data at time period t obtained along a linear orbit $V|_t$: volume to be reconstructed as it existed at time period t w(t): weighting coefficient for a time period t As given in Eq. 5, the net weight given to the first set of projection data $p_L$ from a linear scan obtained over the time period t0 is equal to one minus the weighting coefficient w(t) for the second set of projection data $p_L$ from a linear scan obtained over the time period tm. This is not necessarily the case, and the net weight given to the first set of projection data $p_L$ can be adjusted to, e.g., prevent excessively weighting the first set of projection data $p_L$ if the patient or object moves.

Furthermore, although the weighting coefficient w(t) is described as a function of a time period t, several weighting coefficients may also be provided for each time period t. In other words, the weighting coefficient w(t) may be a function of time, rather than simply a function of the time period t.

The weighting coefficient w(t) also need not simply be a linear interpolation of two points of projection data, as given in Eq. 5. For example, a cubic spline or a polynomial fit using, e.g., three or more points may be performed. In these cases, Eq. 4 simply represents a particular example where the net weight given to the third (and any further) set of projection data $p_L$ from a linear scan is zero.

Returning now to Eq. 4, at the end of a scan, the weighting coefficient w(t) for the second set of projection data $p_L$ obtained over a time period tm can also be set to zero and the weighting coefficient w(t) for the first set of projection data $p_L$ obtained over a time period t0 can also be set to 1, returning to the situation given by Eq. 3.

The successive linear scans illustrated in FIG. 7b may commence a set time interval after the completion of the previous linear scans, or they may be triggered as needed. For example, the projection data from the continuous circular scan will be collected, once per revolution, from the same projection angle as that the linear scan was performed from. By comparing this particular subset of the projection data $p_C$ with a subset of the from projection data $p_L$ obtained from the same position, a measure of movement of the patient or object over time can be made, and the need for a new linear scan determined.

Figure 9:
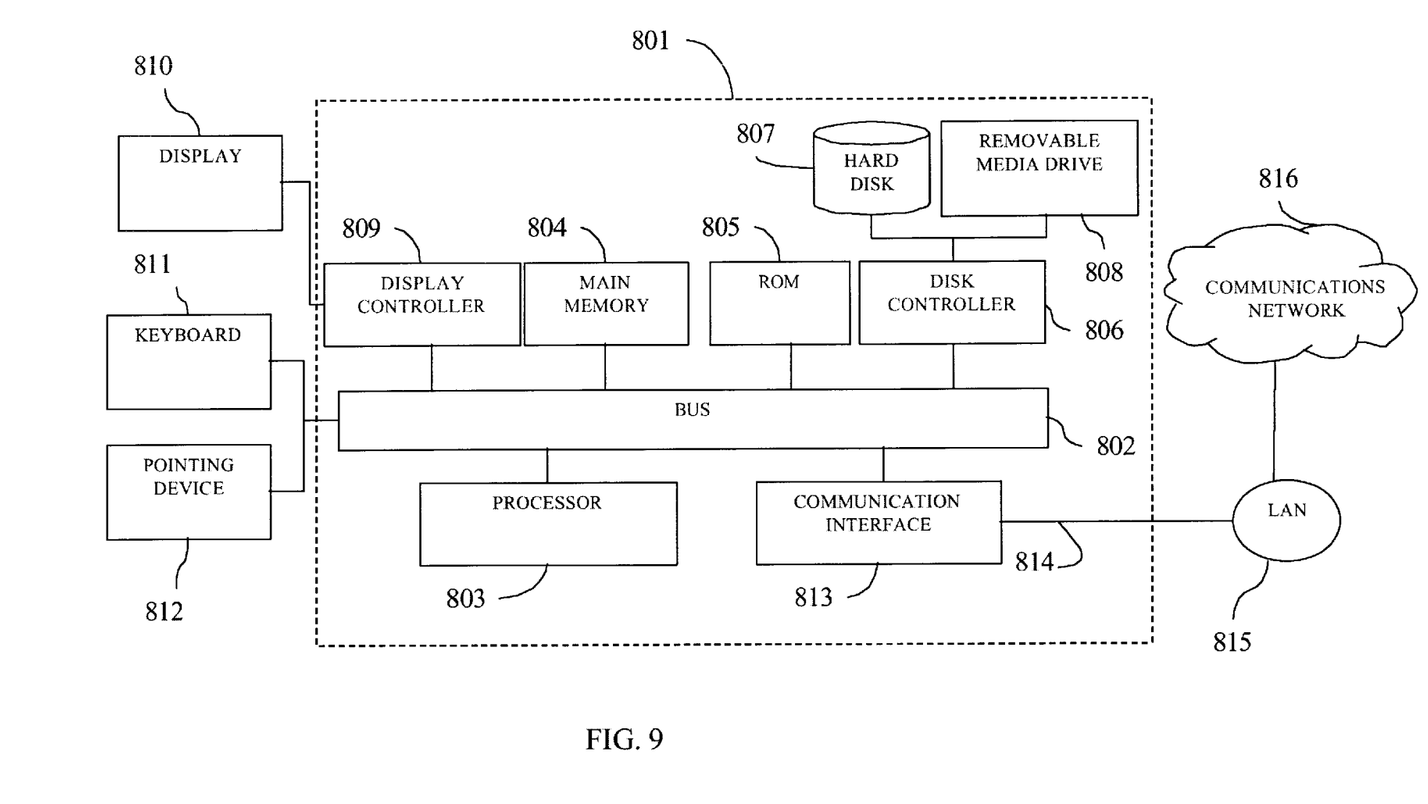
FIG. 9 illustrates a computer system that can perform several different steps of an embodiment of the present invention.

FIG. 8 illustrates a computer system 801 that can perform several steps of an embodiment of the present invention. Computer system 801 includes a bus 802 or other communication mechanism for communicating information, and a processor 803 coupled with bus 802 for processing the information. Computer system 801 also includes a main memory 804, such as a random access memory (RAM) or other dynamic storage device (e.g., dynamic RAM (DRAM), static RAM (SRAM), synchronous DRAM (SDRAM), flash RAM), coupled to bus 802 for storing information and instructions to be executed by processor 803. In addition, main memory 804 may be used for storing temporary variables or other intermediate information during execution of instructions to be executed by processor 803. Computer system 801 further includes a read only memory (ROM) 805 or other static storage device (e.g., programmable ROM (PROM), erasable PROM (EPROM), and electrically erasable PROM (EEPROM)) coupled to bus 802 for storing static information and instructions for processor 803. A hard disk 807 and/or removable media drive 808, such as a magnetic disk or optical disk, is provided and coupled to bus 802 by way of a disk controller 806 for storing information and instructions. Hard disk 807 and/or removable media drive 808 can store raw projection data $p_C$ and/or projection data $p_L$, as well as various weighting coefficients w(t), reconstructed volumes V, and/or instructions for performing the methods of processing projection data obtained along a circular orbit and/or a linear orbit and the methods of the present invention.

The computer system 801 may also include special purpose logic devices (e.g., application specific integrated circuits (ASICs)) or configurable logic devices (e.g., generic array of logic (GAL) or reprogrammable field programmable gate arrays (FPGAs)) that may, e.g., be dedicated to performing the methods of processing projection data obtained along a circular orbit and/or a linear orbit. Other removable media devices (e.g., a compact disc, a tape, and a removable magneto-optical media) or further fixed, high density media drives, may be added to the computer system 801 using an appropriate device bus (e.g., a small computer system interface (SCSI) bus, an enhanced integrated device electronics (IDE) bus, or an ultra-direct memory access (DMA) bus). Such removable media devices and fixed, high density media drives can also store raw projection data $p_C$ and/or projection data $p_L$, as well as various weighting coefficients w(t), reconstructed volumes V, and/or instructions for performing the methods of processing projection data obtained along a circular orbit and/or a linear orbit and the methods of the present invention. The computer system 801 may additionally include a compact disc reader, a compact disc reader-writer unit, or a compact disc juke box, each of which may be connected to the same device bus or another device bus.

Computer system 801 may be coupled via bus 802 to a display 810, such as a cathode ray tube (CRT), for displaying information to a computer user. The display 810 may be controlled by a display or graphics card. The computer system includes input devices, such as a keyboard 811 and a pointing device 812 (e.g., a cursor control), for communicating information and command selections to processor 803. The pointing device 812 (e.g., cursor control), for example, is a mouse, a trackball, or cursor direction keys for communicating direction information and command selections to processor 803 and for controlling cursor movement on the display 810.

The computer system 801 performs a portion or all of the processing steps of the invention in response to processor 803 executing one or more sequences of one or more instructions contained in a memory, such as the main hard disk memory 807. Such instructions may be read into the main hard disk memory 807 from another computer-readable medium, such as removable media drive 808. Thus, either the main hard disk memory 807 or the removable media drive 808 can include instructions for performing the methods of processing projection data obtained along a circular orbit and/or a linear orbit, and the methods of the present invention. One or more processors in a multi-processing arrangement may also be employed to execute the sequences of instructions contained in main hard disk memory 807. In alternative embodiments, hard-wired circuitry may be used in place of or in combination with software instructions. Thus, embodiments are not limited to any specific combination of hardware circuitry and software.

As stated above, the system 801 includes at least one computer-readable medium or memory programmed according to the teachings of the invention and for storing data structures, tables, records, or other data described herein. Examples of computer-readable media are compact discs, hard disks, floppy disks, tape, magneto-optical disks, PROMs (EPROM, EEPROM, Flash EPROM), DRAM, SRAM, SDRAM, etc. Stored on any one or on a combination of computer-readable media, the present invention includes software for controlling the computer system 801, for driving a device or devices for implementing the invention, and for enabling the computer system 801 to interact with a human user. Such software may include, but is not limited to, device drivers, operating systems, development tools, and applications software. Such computer-readable media further includes the computer program product of the present invention for performing all or a portion (if processing is distributed) of the processing performed in implementing the invention.

The computer code devices of the present invention may be any interpreted or executable code mechanism, including but not limited to scripts, interpreters, dynamic link libraries, Java classes, and complete executable programs. Moreover, parts of the processing of the present invention may be distributed for better performance, reliability, and/or cost.

The term "computer-readable medium" as used herein refers to any medium or media that participate in providing instructions to processor 803 for execution. A computer-readable medium may take many forms, including but not limited to, non-volatile media, volatile media, and transmission media. Non-volatile media includes, for example, optical, magnetic disks, and magneto-optical disks, such as hard disk 807 and/or removable media drive 808. Transmission media includes coaxial cables, copper wire and fiber optics, including the wires that comprise bus 802. Transmission media also may also take the form of acoustic or light waves, such as those generated during radio wave and infrared data communications.

Common forms of computer-readable media include, for example, hard disks, floppy disks, tape, magneto-optical disks, PROMs (EPROM, EEPROM, Flash EPROM), DRAM, SRAM, SDRAM, or any other magnetic medium, compact disks (e.g., CD-ROM), or any other optical medium, punch cards, paper tape, or other physical medium with patterns of holes, a carrier wave (described below), or any other medium from which a computer can read.

Various forms of computer-readable media may be involved in carrying out one or more sequences of one or more instructions to processor 803 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to computer system 801 may receive the data on the telephone line and use an infrared transmitter to convert the data to an infrared signal. An infrared detector coupled to bus 802 can receive the data carried in the infrared signal and place the data on bus 802. Bus 802 carries the data to main hard disk memory 807, from which processor 803 retrieves and executes the instructions. The instructions received by main hard disk memory 807 may optionally be stored on a removable media storage device 808 either before or after execution by processor 803.

Computer system 801 also includes a communication interface 813 coupled to bus 802. Communication interface 813 provides a two-way data communication coupling to a communications network 816 that is connected to, e.g., a position controller for an X-ray source and/or detector, as well as to and from the X-ray source and/or detector themselves. For example, communication interface 813 may be a network interface card to attach to any packet switched local area network (LAN). As another example, communication interface 813 may be an asymmetrical digital subscriber line (ADSL) card, an integrated services digital network (ISDN) card or a modem to provide a data communication connection to a corresponding type of telephone line. Wireless links may also be implemented. In any such implementation, communication interface 813 sends and receives electrical, electromagnetic or optical signals that carry digital data streams representing various types of information.

Communications network 816 typically provides data communication through one or more networks to other data devices. For example, communications network 816 may provide a connection to another computer (not shown) through local network 815 (e.g., a LAN) or through equipment operated by a service provider, which provides communication services through a communications network 816. In some embodiments, local network 815 and communications network 816 preferably use electrical, electromagnetic, or optical signals that carry digital data streams from, e.g., a position controller for an X-ray source and/or detector, as well as to and from the X-ray source and/or detector themselves. The signals through the various networks and the signals on network link 814 and through communication interface 813, which carry the digital data to and from computer system 801, are exemplary forms of carrier waves transporting the information. Computer system 801 can transmit notifications and receive data, including program code, through the network(s), network link 814 and communication interface 813.

Numerous modifications and variations of the present invention are possible in light of the above teachings. It is therefore to be understood that within the scope of the appended claims, the invention may be practiced otherwise than as specifically described herein.

LIST OF REFERENCES

1: L. A. Feldkamp, L. C. Davis, J. W. Kress, "Practical cone-beam algorithm," J. Opt. Soc. Am., 1(6), pp. 612–619, 1984.

2a: H. Kudo and T. Saito, "Three-dimensional helical-scan computed tomography using cone-beam projections," IEICE (D-II) J74-D-II, 1108–1114 (1991); The technique of literature 1 is applied to helical scan.

2b: Katsuyuki Taguchu, "X-ray Computerized Tomography Apparatus", Japanese Patent Laid-Open No. 19425/1997, Jan. 21, 1997; The technique of literature 1 is applied to a cylindrical detector and helical scan.

3a: H. Kudo and T. Saito, "Derivation and implementation of a cone-beam reconstruction algorithm for nonplanar orbits," IEEE Trans. Med. Imag. MI-13, pp. 186–195, 1994; Cone beam reconstruction by scan of line and circular orbits.

3b: H. Kudo and T. Saito, "An extended completeness condition for exact cone-beam reconstruction and its application," Conf. Rec. 1994 IEEE Med. Imag. Conf. (Norfolk, Va.) (New York: IEEE) 1710–14; Cone beam reconstruction by scan of line and circular orbits.

4: M. Defrise and R. Clack, "A cone-beam reconstruction algorithm using shift-variant filtering and cone-beam backprojection," IEEE Trans. Med. Imag., MI-13, pp. 186–195, 1994; Cone beam reconstruction by scan of line and circular orbits.

5: Patent by Aradate, Saito and Miyazaki (number not known, filed in latter half of 1999); Basic concept of 4D-CT. Feldkamp reconstruction by cutting out from continuous revolutions.

6: D. L. Parker, "Optimal short scan convolution reconstruction for fan-beam CT," Med. Phys. 9, pp. 254–257, 1982

7: C. Crawford and K. F. King, "Computed tomography scanning with simultaneous patient translation," Med. Phys. 17, pp. 967–982, 1990

8: M. D. Silver, "A method for including redundant data in computed tomography," Med. Phys. 27, pp. 773–774, 2000.

What is claimed as new and desired to be secured by Letters Patent of the United States is:

1. A computed tomography apparatus comprising:

an X-ray source configured to expose a subject to a cone-shaped beam of X-rays;

an X-ray detector including a plurality of detector elements and configured to receive a portion of said cone-shaped beam of X-rays emitted from said X-ray source, said portion having passed through a subject;

a data acquisition device configured to collect a first projection data set at a circular time along a circular trajectory of the cone-shaped X-rays around said subject and a second projection data set at a second time set along a second trajectory of the cone-shaped X-rays relative to said subject, said second trajectory being different from said circular trajectory, said first projection data set being collected after said second projection data set; and a reconstruction device configured to reconstruct a volume at said circular time from said second projection data set and said first projection data set.

2. The apparatus according to claim 1, wherein said second trajectory comprises at least one of a helical trajectory and a line trajectory.

3. The apparatus according to claim 1, wherein said reconstruction device is configured to correct an approximated volume data reconstructed from the first projection data using the second projection data set.

4. The apparatus according to claim 3, wherein said reconstruction device is configured to add the second projection data set to the approximated volume data.

5. The apparatus according to claim 3, wherein said data acquisition device is configured to obtain said first projection data set by revolving said X-ray source one or more times about said subject.

6. The apparatus according to claim 1, wherein said reconstruction device comprises a weighting device configured to weight overlapping projection data from said first projection data set to reconstruct said volume.

7. The apparatus according to claim 1, wherein said data acquisition device is configured to obtain said second projection data set at a regular time interval.

8. The apparatus according to claim 1, wherein said data acquisition device is configured to collect said second projection data set after said first projection data set.

9. A computed tomography apparatus comprising:
an X-ray source configured to expose a subject to a cone-shaped beam of X-rays;
an X-ray detector including a plurality of detector elements and configured to receive a portion of said cone-shaped beam of X-rays emitted from said X-ray source, said portion having passed through a subject;
a data acquisition device configured to collect a first projection data set at a circular time along a circular trajectory of the cone-shaped X-rays around said subject and a second projection data set at a second time set along a second trajectory of the cone-shaped X-rays relative to said subject, said second trajectory being different from said circular trajectory; and
a reconstruction device configured to reconstruct a volume at said circular time from said second projection data set and said first projection data set,
wherein said second trajectory comprises a plurality of translations.

10. The apparatus according to claim 9, wherein a first translation of said plurality of translations is performed prior to said collection of said first projection data set and a second translation of said plurality of translations is performed after said collection of said first projection data set.

11. The apparatus according to claim 10, wherein said data acquisition device is configured to obtain said first projection data set by revolving said X-ray source one or more times about said subject.

12. A computed tomography apparatus comprising:
an X-ray source configured to expose a subject to a cone-shaped beam of X-rays;
an X-ray detector including a plurality of detector elements and configured to receive a portion of said cone-shaped beam of X-rays emitted from said X-ray source, said portion having passed through a subject;
a data acquisition device configured to collect a first projection data set at a circular time along a circular trajectory of the cone-shaped X-rays around said subject and a second projection data set at a second time set along a second trajectory of the cone-shaped X-rays relative to said subject, said second trajectory being different from said circular trajectory;
a reconstruction device configured to reconstruct a volume at said circular time from said second projection data set and said first projection data set;
a display device configured to display the volume data in a p redetermined display form; and
a control device configured to control said data acquisition device, said reconstruction device, and said display device such that said reconstruction device reconstructs said volume in a time less than said circular time and said display device displays the volume data after a fixed delay after said reconstruction device reconstructs said volume.

13. A computed tomography apparatus comprising:
an X-ray source configured to expose a subject to a cone-shaped beam of X-rays;
an X-ray detector including a plurality of detector elements and configured to receive a portion of said cone-shaped beam of X-rays emitted from said X-ray source, said portion having passed through a subject;
a data acquisition device configured to collect a first projection data set at a circular time along a circular trajectory of the cone-shaped X-rays around said subject and a second projection data set at a second time set along a second trajectory of the cone-shaped X-rays relative to said subject, said second trajectory being different from said circular trajectory; and
a reconstruction device configured to reconstruct a volume at said circular-time from said second projection data set and said first projection data set,
wherein said reconstruction device comprises a weighting device configured to weight overlapping projection data from said first projection data, said overlapping projection data spanning less than 360° and more than 180° plus fan angle.

14. A computed tomography apparatus comprising:
an X-ray source configured to expose a subject to a cone-shaped beam of X-rays;
an X-ray detector including a plurality of detector elements and configured to receive a portion of said cone-shaped beam of X-rays emitted from said X-ray source, said portion having passed through a subject;
a data acquisition device configured to collect a first projection data set at a circular time along a circular trajectory of the cone-shaped X-rays around said subject and a second projection data set at a second time set along a second trajectory of the cone-shaped X-rays relative to said subject, said second trajectory being different from said circular trajectory;
a reconstruction device configured to reconstruct a volume at said circular time from said second projection data set and said first projection data set;
a display device configured to display the volume data in a predetermined display form; and
a control device configured to control said data acquisition device, said reconstruction device, and said display device such that said reconstruction device reconstructs said volume in a time less than said circular time and said display device displays the volume data after a fixed delay after said reconstruction device reconstructs said volume.

15. A computed tomography apparatus comprising:
a first data acquisition device configured to obtain, along a line trajectory, a first projection data set of cone-shaped X-rays having passed through a subject;
a second data acquisition device configured to obtain, along a circular trajectory, a second projection data set of the cone-shaped X-rays having passed through said subject through relative revolution of said cone-shaped X-rays and said subject; and a generating device configured to reconstruct a volume and obtain a scanogram;

said volume reconstructed from said first projection data set and at least a part of said second projection data set; and said scanogram obtained from at least a part of said first projection data set, at least one of a position and a range of said at least a part of said second projection data set determined from said scanogram.

16. A method of imaging a volume, comprising:

collecting a first data set along a substantially circular orbit about a subject, said first data set comprising at least one scan data subset performed over a time period centered on a circular time t, said scan data subset comprising a minimal complete data set;

collecting a second data set along a second orbit over a second data set time period; and reconstructing said volume as said volume existed at said circular time t using said scan data subset of said first data set and said second data set.

17. The method according to claim 16, wherein said collecting a first data set step is performed prior to said collecting a second data set step.

18. The method according to claim 16, wherein said collecting a second data set comprises scanning along a linear orbit over said second data set time period.

19. The method according to claim 16, wherein said collecting a second data set comprises scanning along a helical orbit over said second data set time period.

20. The method according to claim 16, further comprising:

selecting a second scan data subset from said first data set collected over a second time period centered on a second circular time t2; and reconstructing said volume as said volume existed at said second circular time t using said second scan data subset of said first data set and said second data set.

21. The method according to claim 20, further comprising repeating said selecting and reconstructing steps for a further scan data subset from said first data set collected over a further time period centered on a further circular time tf.

22. A method of imaging a volume, comprising:

collecting a first data set along a substantially circular orbit about a subject, said first data set comprising at least one scan data subset performed over a time period centered on a circular time t, collecting a second data set along a second orbit over a second data set time period; and reconstructing said volume as said volume existed at said circular time t using said scan data subset of said first data set and said second data set, wherein said scan data subset comprises a complete revolution data set.

23. A method of imaging a volume, comprising:

collecting a first data set along a substantially circular orbit about a subject, said first data set comprising at least one scan data subset performed over a time period centered on a circular time t, collecting a second data set along a second orbit over a second data set time period;

reconstructing said volume as said volume existed at said circular time t using said scan data subset of said first data set and said second data set;

collecting a third data set along said second orbit over a third data set time period; and weighting at least one third data set point and at least one second data set point to yield a weighted second data set point used in said reconstructing step with said scan data subset of said first data set.

24. The method according to claim 23, wherein said weighting step comprises interpolating said at least one third data set point and at least one second data set point to yield an interpolated second data set point used in said reconstructing step with said scan data subset of said first data set.

25. The method according to claim 23, further comprising repeating said collecting and weighting steps with a further data set collected over a further data set time period.

26. A method of imaging a volume, comprising:

collecting a first data set along a substantially circular orbit about a subject, said first data set comprising at least one scan data subset performed over a time period centered on a circular time t, collecting a second data set along a second orbit over a second data set time period; and reconstructing said volume as said volume existed at said circular time t using said scan data subset of said first data set and said second data set, wherein said scan data subset comprises a partial revolution data set spanning more than said minimal complete data set.

27. A computer-readable medium containing program instructions for execution on a computer system, which when executed by the computer system, cause the computer system to perform the method recited in any one of claims 16, and 22 to 19.

28. A device comprising:

means for collecting a first data set along a substantially circular orbit about a subject, collecting a second data set along a second orbit over a second data set time period, and collecting a third data set along said second orbit over a third data set time period, said first data set comprising at least one scan data subset performed over a time period centered on a circular time t;

means for reconstructing said volume as said volume existed at said circular time t using said scan data subset of said first data set and said second data set; and means for weighting at least one third data set point and at least one second data set point to yield a weighted second data set point used in said reconstructing step with said scan data subset of said first data set.

29. The device according to claim 28, further comprising:

means for selecting a second scan data subset from said first data set collected over a second time period centered on a second circular time t2, wherein said means for reconstructing comprises mean for reconstructing said volume as said volume existed at said second circular time t using said second scan data subset of said first data set and said second data set.

* * * * *